United States Patent
Raslambekov

(10) Patent No.: US 10,426,575 B1
(45) Date of Patent: Oct. 1, 2019

(54) SYSTEMS AND METHODS FOR DETERMINING AN ORTHODONTIC TREATMENT

(71) Applicant: 3D MED AG, Zug (CH)

(72) Inventor: Islam Khasanovich Raslambekov, Moscow (RU)

(73) Assignee: 3D MED AG, St. Moritz (CH)

( * ) Notice: Subject to any disclaimer, the term of this patent is extended or adjusted under 35 U.S.C. 154(b) by 0 days.

(21) Appl. No.: 16/132,995

(22) Filed: Sep. 17, 2018

(51) Int. Cl.
*A61C 3/00* (2006.01)
*A61C 7/00* (2006.01)
*G16H 50/50* (2018.01)
*A61C 9/00* (2006.01)

(52) U.S. Cl.
CPC ............ *A61C 7/002* (2013.01); *A61C 9/0046* (2013.01); *G16H 50/50* (2018.01); *A61C 2007/004* (2013.01)

(58) Field of Classification Search
CPC . A61C 7/002; A61C 9/0046; A61C 2007/004; G16H 50/50; G06F 19/30; G06F 19/36; G06F 19/34; G06Q 50/22; G06Q 50/24
See application file for complete search history.

(56) References Cited

U.S. PATENT DOCUMENTS

| | | |
|---|---|---|
| 6,632,089 B2 | 10/2003 | Rubbert et al. |
| 8,417,366 B2 | 4/2013 | Getto et al. |
| 9,161,824 B2 | 10/2015 | Chishti et al. |
| 2002/0006597 A1 | 1/2002 | Andreiko et al. |
| 2002/0015934 A1* | 2/2002 | Rubbert ............... A61C 7/00 433/29 |

(Continued)

FOREIGN PATENT DOCUMENTS

CN       102727316 B       9/2015

(Continued)

OTHER PUBLICATIONS

James Mah et al. "Computer-assisted orthodontic treatment: The SureSmile process", AJO-DO Jul. 2001; vol. 120, Issue 1, pp. 85-87, Los Angeles, Califordia, USA; DOI: 10.1067/mod.2001. 117686.

(Continued)

*Primary Examiner* — Nicholas D Lucchesi
(74) *Attorney, Agent, or Firm* — BCF LLP

(57) ABSTRACT

Determining an orthodontic treatment having sequential treatment steps defining treatment intervals therebetween. The method comprises obtaining a segmented 3D model of teeth; obtaining start and desired end positions of each tooth; determining an initial number of sequential treatment steps; for each tooth and for each treatment interval, determining a root force imposed on a root portion of the given tooth by a given orthodontic appliance; in response to the root force of each tooth not exceeding a predetermined threshold value, determining that the determined initial number of sequential treatment steps is the determined orthodontic treatment; and in response to the root force exceeding the predetermined threshold value, iteratively decreasing the initial distance of each treatment interval to provide a revised number of sequential treatment steps, and re-calculating the root force until it is determined that the root force of each tooth does not exceed the predetermined threshold value.

20 Claims, 11 Drawing Sheets

(56) References Cited

U.S. PATENT DOCUMENTS

| | | | |
|---|---|---|---|
| 2006/0105286 A1* | 5/2006 | Raby | A61C 7/12 |
| | | | 433/24 |
| 2006/0223022 A1* | 10/2006 | Solomon | A61C 7/08 |
| | | | 433/6 |
| 2006/0223023 A1 | 10/2006 | Lai et al. | |
| 2006/0263740 A1 | 11/2006 | Sporbert et al. | |
| 2006/0275731 A1* | 12/2006 | Wen | A61C 7/00 |
| | | | 433/24 |
| 2006/0275736 A1* | 12/2006 | Wen | A61C 9/00 |
| | | | 433/213 |
| 2008/0096151 A1 | 4/2008 | Cinader et al. | |
| 2016/0055312 A1* | 2/2016 | Badawi | A61C 7/002 |
| | | | 703/11 |
| 2016/0067013 A1 | 3/2016 | Morton et al. | |
| 2016/0120616 A1* | 5/2016 | Viazis | A61C 7/14 |
| | | | 433/24 |
| 2017/0128168 A1* | 5/2017 | Bindayel | A61B 90/98 |

OTHER PUBLICATIONS

SureSmile technology, information retrieved from https://www.suresmile.com/ on Sep. 6, 2018.

European Search Report dated Mar. 13, 2019 in respect of the European patent application No. 18194960.3.

\* cited by examiner

SYSTEMS AND METHODS FOR DETERMINING AN ORTHODONTIC TREATMENT

FIELD

The present technology relates to systems and methods for determining an orthodontic treatment.

BACKGROUND

In orthodontics, treatments for achieving alignment of malposed teeth in a patient include applying orthodontic appliances to the patient's teeth, such as a pre-shaped orthodontic wire attached to brackets which are themselves attached to the teeth. The wires, also known as archwires, are typically made from shape memory alloys which have the ability to recover their shape after being deformed. This re-shaping occurs at a predetermined temperature, usually around 38° C. Shape memory alloys used in orthodontic archwires include nickel-titanium alloys (e.g. Nitinol™), beta-titanium alloys, and copper nickel-titanium alloys.

The wire is typically pre-shaped into a desired shape by forming bends at desired positions and with desired angles, heating under tension, and super-cooling. The heating step typically comprises electric heating. Once pre-shaped, the wire is attached to the brackets by bending its shape to conform to the general shape of the malposed teeth. When the wire warms to mouth temperature it reverts to its original shape thereby exerting a force on the teeth to which it is attached to move them.

A typical orthodontic treatment comprises a number of consecutive treatment steps in which wires of different shapes and/or stiffness may be used for applying different forces to the teeth as the alignment progresses. In some cases, the treatment steps may be classified as an aligning stage, a levelling stage, a working stage, a finishing stage and a settling stage. In some cases, the treatment stages comprise an initial stage, a transitional stage and a finishing stage. The treatment stages may include an imposed orthodontic action such as rotation or linear movement of one or more teeth, development of the arch form, a levelling of the arches, torque control or simple retention of the position. Generally, the earlier treatment stages apply more gentle forces compared to the main treatment stages. Thicker wires may be used for the more aggressive repositioning phase.

In one prior art system, U.S. Pat. No. 9,161,824, a computer-automated system for creating a plan for orthodontic repositioning of a patient's teeth is described. A treatment plan is determined based on a digital model of the individual teeth, and an initial and final position of each tooth. The number of desired treatment stages can be set by the user of the software. The user may also define "key frames" by selecting an intermediate state and making changes to component position(s). In some described embodiments, unless instructed otherwise, the software automatically linearly interpolates between all user-specified positions (including the initial position, all key frame positions, and the target position). The operations within each key frame can be done independently to each component. In some described implementations, non-linear interpolation is used instead of or in addition to linear interpolation to a construct a treatment path among key frames. However, the technology described in U.S. Pat. No. 9,161,824 still requires a clinician's input and judgement in determining the treatment plan. Specifically, the clinician is required to determine the number of key stages, a treatment within each key stage, whether to apply a linear or a non-linear interpolation to the treatment stages, etc.

It is an object of the present technology to ameliorate at least some of the inconveniences present in the prior art.

SUMMARY

Embodiments of the present technology have been developed based on developers' appreciation of certain shortcomings associated with the existing systems for determining an orthodontic treatment.

Embodiments of the present technology have been developed based on the developers' observation that a number of factors must be considered when determining the treatment steps. Discomfort to the patient is a consideration and it is desirable to minimize the number of treatment steps and the total treatment time. Cost is also a consideration, and each treatment step adds cost. Therefore, an efficient treatment time with as few changes of wire or bracket is desirable. However, a shorter treatment time may necessitate that the applied forces to the teeth are higher in order to move them within a shorter time frame. This can also be uncomfortable for the patient, and risk mechanical damage to the teeth.

Although some recommendation tables exist for the treatment steps, ultimately the chosen treatment path is based on the clinician's experience and judgment. This means that outcomes between clinicians are variable. A further confounding factor is that the actual behaviour of the teeth may be very different from what the clinician has planned (i.e. the desired result and orientation of the teeth that the orthodontic treatment is supposed to render).

From one aspect, there is provided a method for determining an orthodontic treatment having a number of sequential treatment steps with a given orthodontic appliance, the sequential treatment steps defining treatment intervals therebetween, the method executable by a processor of a computer system, the method comprising: obtaining a segmented 3D model of a plurality of teeth of a patient, the segmented 3D model of each tooth of the plurality of teeth including at least crown portion data; obtaining a start position and a desired end position of each tooth of the plurality of teeth; determining an initial number of sequential treatment steps to move each tooth of the plurality of teeth from the start position to the desired end position, the initial number of sequential treatment steps being based on an initial distance of each treatment interval; for each tooth of the plurality of teeth, and for each treatment interval, determining a root force imposed on a root portion of the given tooth by the given orthodontic appliance; and selectively executing: in response to the root force of each tooth of the plurality of teeth not exceeding a predetermined threshold value, determining that the determined initial number of sequential treatment steps is the determined orthodontic treatment; and in response to the root force, for any one of the teeth of the plurality of teeth, exceeding the predetermined threshold value, iteratively decreasing the initial distance of each treatment interval to provide a revised number of sequential treatment steps, and for each one of the determined revised number of sequential treatment steps re-calculating the root force imposed on the root portion of each tooth by the given orthodontic appliance, until it is determined that the root force, of each tooth of the plurality of teeth, does not exceed the predetermined threshold value.

In certain embodiments, determining the root force imposed on the root portion of the given tooth in the given treatment interval comprises: simulating movement of the given tooth within the given treatment interval, based on simulation of the movement of the given tooth from the start position to the desired end position based on the segmented 3D model of the plurality of teeth; determining an impact force of the given orthodontic appliance used during the given treatment interval on the given tooth, based on the simulated movement of the given tooth within the given treatment interval; and determining the root force imposed on the root portion of the given tooth, based on the determined impact force and an anatomical consideration of the root portion of the given tooth.

In certain embodiments, the re-calculating the root force imposed on the root portion of each tooth by the given orthodontic appliance comprises: determining a revised impact force of the given orthodontic appliance used during the given treatment interval on the given tooth, based on the simulated movement of the given tooth within the given treatment interval; and determining a revised root force imposed on the root portion of the given tooth, based on the revised impact force and the anatomical consideration of the root portion of the given tooth.

In certain embodiments, the anatomical consideration of the root portion of the given tooth comprises root portion data including one or more of: a geometry of the root portion, an indication of a length of the root portion, crown portion topography, root portion topography, root portion surface area, and type of tooth.

In certain embodiments, the method further comprises obtaining the root portion data by obtaining CT scan data of the plurality of teeth, segmenting the CT scan data to separate the individual teeth, and parsing the CT scan data to separate crown portion data from root portion data.

In certain embodiments, the obtaining the segmented 3D model of the plurality of teeth comprises: obtaining 3D optical image data of the plurality of teeth, and digitally separating each tooth of the plurality of teeth in the 3D optical image data to obtain the segmented 3D image data of the plurality of teeth.

In certain embodiments, the impact force of the given orthodontic appliance is determined based on Finite Element Method (FEM) modelling.

In certain embodiments, the FEM modelling comprises imposing boundary conditions which reflect the interaction (or deformation) of an orthodontic appliance with the teeth, caused by contact of the teeth with the orthodontic appliance, during a simulation of the movement of the teeth from the start position to the desired end position. The orthodontic appliance can be any type of orthodontic appliance such as: lingual arches, transpalatal bars, biteplanes etc.

In certain embodiments, the impact force of the given orthodontic appliance is based on one or more of: orthodontic appliance material property, orthodontic appliance configuration, and orthodontic appliance method of manufacture.

In certain embodiments, the root force comprises an average force imposed on periodontal ligaments around an entirety of the given tooth root portion.

In certain embodiments, the decreasing the initial distance comprises decreasing the initial distance by an amount proportional to an excess amount of the determined root force above the predetermined threshold.

In certain embodiments, the method further comprises determining intermediate collisions between adjacent teeth in the plurality of teeth for each treatment interval between each sequential treatment step of the initial number of sequential steps, the determining intermediate collisions being based on the determined simulated movement of each tooth.

In certain embodiments, the method further comprises displaying the determined intermediate collisions on a screen connected to the computer system, or sending instructions to display the intermediate collisions on a screen.

In certain embodiments, the method further comprises one or both of: displaying the determined orthodontic treatment on a screen connected to the computer system; and sending production instructions to the orthodontic appliance manufacture apparatus to generate the orthodontic appliance according to the determined orthodontic treatment.

In certain embodiments, the obtaining a start position and a desired end position of each tooth of the plurality of teeth comprises defining the start position and the desired end position of each tooth as an x, y, z coordinate. In certain embodiments, the initial distance is about 200 microns.

From another aspect, there is provided a system for determining an orthodontic treatment having a number of sequential treatment steps with a given orthodontic appliance, the system comprising a computer system having a processor arranged to execute a method comprising: obtaining a segmented 3D model of a plurality of teeth of a patient, the segmented 3D model of each tooth of the plurality of teeth including at least crown portion data; obtaining a start position and a desired end position of each tooth of the plurality of teeth; determining an initial number of sequential treatment steps, the initial number of sequential treatment steps defining treatment intervals therebetween, to move each tooth of the plurality of teeth from the start position to the desired end position, the initial number of sequential treatment steps being based on an initial distance of each treatment interval; for each tooth of the plurality of teeth, and for each treatment interval, determining a root force imposed on a root portion of the tooth by the given orthodontic appliance; selectively executing: in response to the root force, of each tooth of the plurality of teeth, not exceeding a predetermined threshold value, determining that the determined initial number of sequential treatment steps is the determined orthodontic treatment; and in response to the root force, for any one of the teeth of the plurality of teeth, exceeding the predetermined threshold value, iteratively decreasing the initial distance of each treatment interval to provide a revised number of sequential treatment steps, and for each one of the determined revised number of sequential treatment steps re-calculating the root force imposed on the root portion of each tooth by the given orthodontic appliance, until it is determined that the root force, of each tooth of the plurality of teeth, does not exceed the predetermined threshold value.

In certain embodiments, the system further comprises one or more of: an imaging device communicable with the computer system for providing image data comprising at least crown portion data of the plurality of teeth, and orthodontic manufacturing apparatus communicable with the computer system for making at least a portion of the orthodontic appliance.

In certain embodiments, the imaging device is one or more of an intra-oral scanner for providing crown portion data of the plurality of teeth, and a CT scanner for providing root portion data of the plurality of teeth.

In certain embodiments, the orthodontic manufacturing apparatus is one or more of a 3D printer, an archwire forming apparatus, and an archwire bending apparatus.

In certain embodiments, the system is further arranged to carry out any one or more of the method steps as described above. In certain embodiments, determining the root force imposed on the root portion of the given tooth in the given treatment interval comprises: simulating movement of the given tooth within the given treatment interval, based on simulation of the movement of the tooth from the start position to the desired end position based on the segmented 3D model of the plurality of teeth; determining an impact force of the given orthodontic appliance used during the given treatment interval on the given tooth, based on the simulated movement of the given tooth within the given treatment interval; and determining the root force imposed on the root portion of the given tooth, based on the determined impact force and an anatomical consideration of the root portion of the given tooth.

In certain embodiments, the re-calculating the root force imposed on the root portion of each tooth by the given orthodontic appliance comprises: determining a revised impact force of the given orthodontic appliance used during the given treatment interval on the given tooth, based on the simulated movement of the given tooth within the given treatment interval; and determining a revised root force imposed on the root portion of the given tooth, based on the revised impact force and the anatomical consideration of the root portion of the given tooth.

In certain embodiments, the number of determined orthodontic treatment steps is an optimal number of orthodontic treatment steps. This can provide orthodontic treatment plans which achieve a balance between minimizing patient discomfort and cost, whilst also minimizing any potential damage to the patient's teeth and periodontal ligaments.

In certain embodiments, the determined orthodontic treatment plan reduces, minimizes or eliminates a clinician's input into the process for determining the orthodontic treatment plan. This automation of the process may have certain advantages, in certain embodiments, of providing improved consistency of achieved orthodontic result between clinicians, an improvement of the orthodontic result itself (i.e. the optimization), as well as reducing a time required to plan orthodontic treatments.

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

It should be noted that, unless otherwise explicitly specified herein, the drawings are not to scale.

DETAILED DESCRIPTION

Certain aspects and embodiments of the present technology, are directed to methods and systems for determining an orthodontic treatment. Broadly, certain aspects and embodiments of the present technology comprise a computer implemented method for determining an optimized orthodontic treatment which minimizes, reduces or avoids the problems noted with the prior art.

Certain aspects and embodiments of the present technology provide methods and systems that determine an orthodontic treatment whilst taking into account a pressure on periodontal ligaments in order to avoid damage to the teeth and ligaments and within patient comfort levels. The technology may be at least partially automated so as to minimize an input of the clinician in developing a treatment plan.

Figure 1:
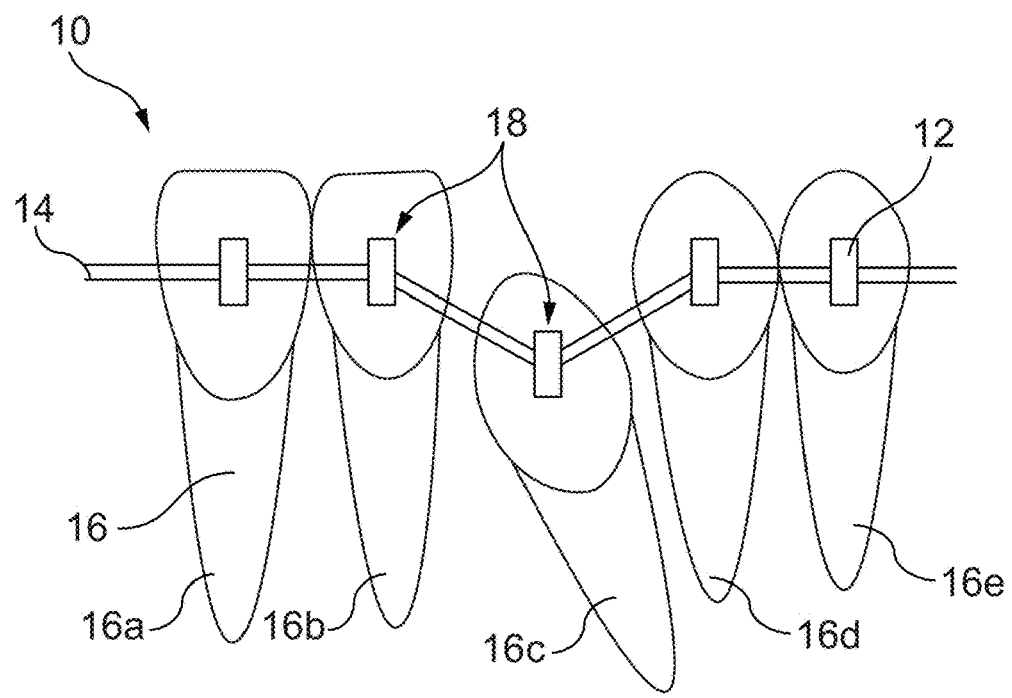
FIG. 1 is a schematic illustration of an orthodontic appliance attached to five teeth of a plurality of teeth of a patient.
Figure 2:
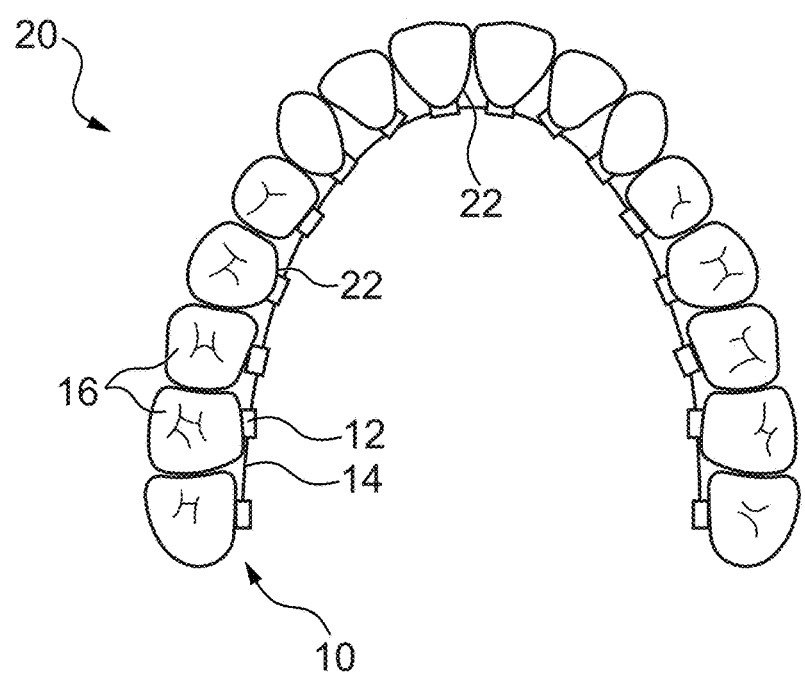
FIG. 2 is a schematic illustration of a lower archform of the patient of FIG. 1 showing the orthodontic appliance of FIG. 1 attached thereto.

Referring initially to FIGS. 1 and 2, there is shown an example orthodontic appliance 10 to which aspects and embodiments of the present technology can be applied. In this embodiment, the orthodontic appliance 10 comprises brackets 12 and an archwire 14. The archwire 14 is made of a shape memory alloy such as Nitinol™, but can also be made of any other shape memory alloy or material with elastic properties. The brackets 12 are provided on teeth 16 (shown individually as 16a, 16b, 16c, 16d, 16e), and the archwire 14 extends between, and is connected to, each of the brackets 12. As illustrated, the maloclusion is misalignment of the tooth 16c for which the treatment plan as illustrated is an upward movement to align the tooth 16c with neighbouring the teeth 16a, 16b, 16d, 16e.

As can be seen, the archwire 14 of FIG. 1 has bends 18 which will gradually move towards an aligned position when installed in a mouth of patient due to the shape memory effect of the archwire 14. This will apply a force on the tooth 16c to move it upwardly.

In FIG. 2, the orthodontic appliance 10 has been applied to all the teeth 16 of a lower jaw 20, with the brackets 12 being attached to an internal surface 22 of the teeth 16.

It will be appreciated that the present technology can be applied to different types, shapes, sizes and configurations of orthodontic appliances 10 such as, without limitation, multi-strand wires, strips, retainers, and plates. Furthermore, the bends 18 in the archwire 14 may comprise rounded corners or loops. It will also be appreciated that the orthodontic appliance 10 may be used for treating any type of teeth misalignment or malocclusion, including but not limited to closing gaps ("space closure"), creating/widening gaps, tooth rotation, tooth intrusion/extrusion, and translation, to name a few.

Figure 3:
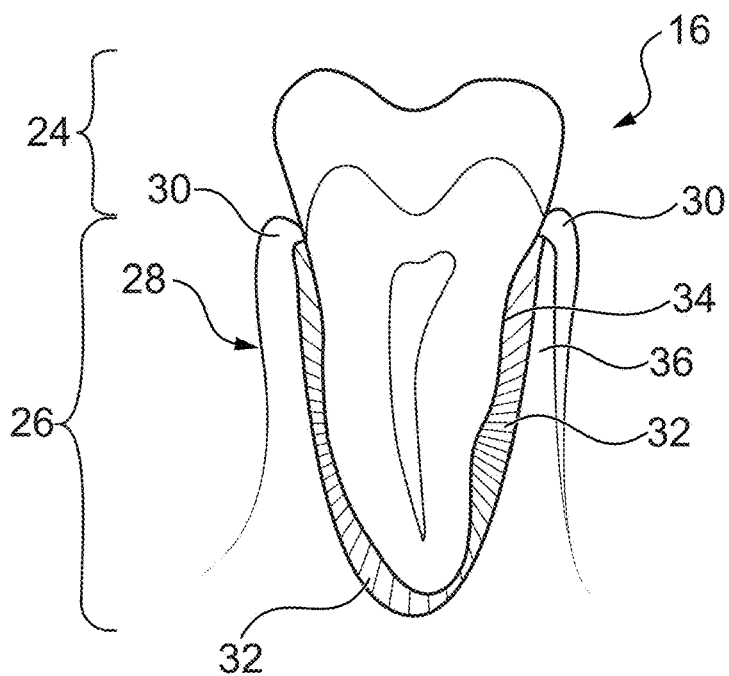
FIG. 3 is a schematic illustration of a cross-section of one tooth of the plurality of teeth of FIG. 1 or FIG. 2 showing internal components.
Figure 4:
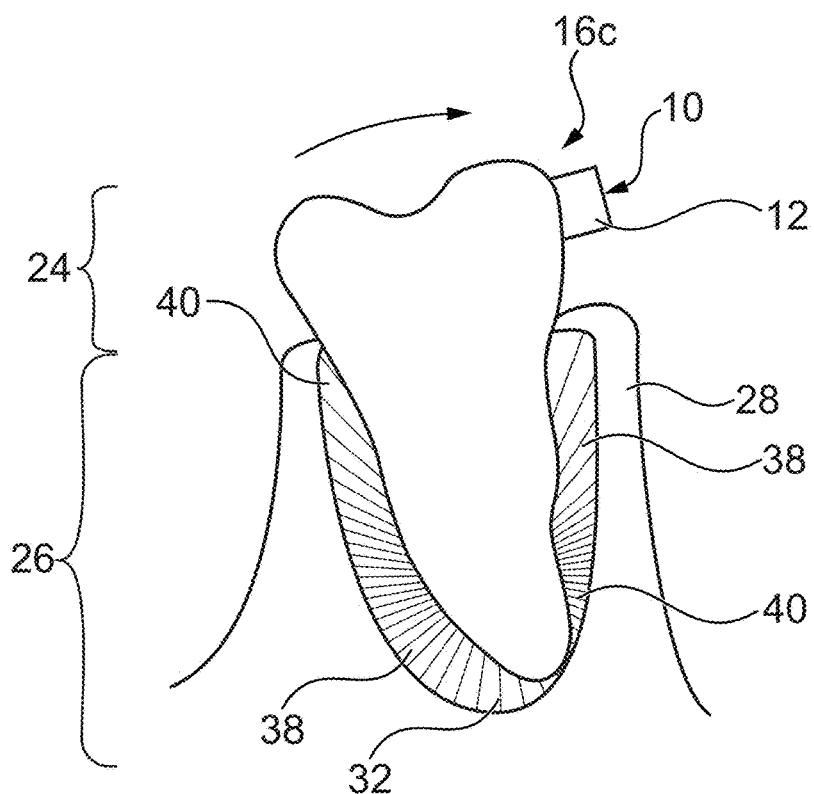
FIG. 4 is the tooth of FIG. 3 and including the orthodontic appliance of FIG. 1.

FIG. 3 shows a schematic of one of the teeth 16 of FIG. 1 or FIG. 2 and showing some of the internal structures of the tooth and the surrounding tissues. FIG. 4 shows the same tooth 16, such as the tooth 16c, when under the influence of a force from the orthodontic appliance 10 to correct the positioning of the tooth 16c and in which the stresses and strains in the surrounding tissues are shown. The tooth 16 comprises a crown portion 24 and a root portion 26. Tissues 28 surrounding and supporting the teeth 16 are generally called the periodontium and include the gingiva 30, periodontal ligament 32, cementum 34 and alveolar bone 36. The periodontal ligament 32 is connective tissue that surrounds the root portion 26 and attaches it to the alveolar bone 36. As can be seen, the effect of the orthodontic appliance 10 (applying force in the direction of the arrow) on the tooth 16c in FIG. 4 is compression of the periodontal ligaments 32 on compressed portions 38 of the root portion 26 and tension of the periodontal ligaments 32 on portions under tension 40 of the root portion 26. This causes bone remodelling around the tooth 16c, with bone resorption occurring on the compressed portion 38 and bone deposition occurring on the portion under tension 40.

In certain orthodontic treatment plans, there are sequential treatment steps in which different orthodontic appliances 10 are applied to the teeth 16 at each treatment step to apply different forces. In some orthodontic treatment plans, there is an initial stage where the teeth 16 are first treated for leveling and alignment. If the orthodontic appliance comprises brackets 12 and archwires 14, archwires 14 which generate a continuous and light force over a relatively longer period of time are generally preferred for this initial stage. In other stages, a stronger force may be required for a relatively shorter period. The material type and diameter of the archwire 14 influences the forces applied to the teeth 16. Generally, archwires 14 with a broader diameter exert a higher force than narrower archwires 14. Material properties such as strength, stiffness and elasticity, as well as shape memory properties also influence the forces applied to the teeth. Therefore, there are many parameter combinations to consider when designing the orthodontic treatment plan.

Aspects and embodiments of the present technology determine orthodontic treatment steps, using a computer-implemented system 100 and method 300, taking into account these parameter combinations.

Figure 5:
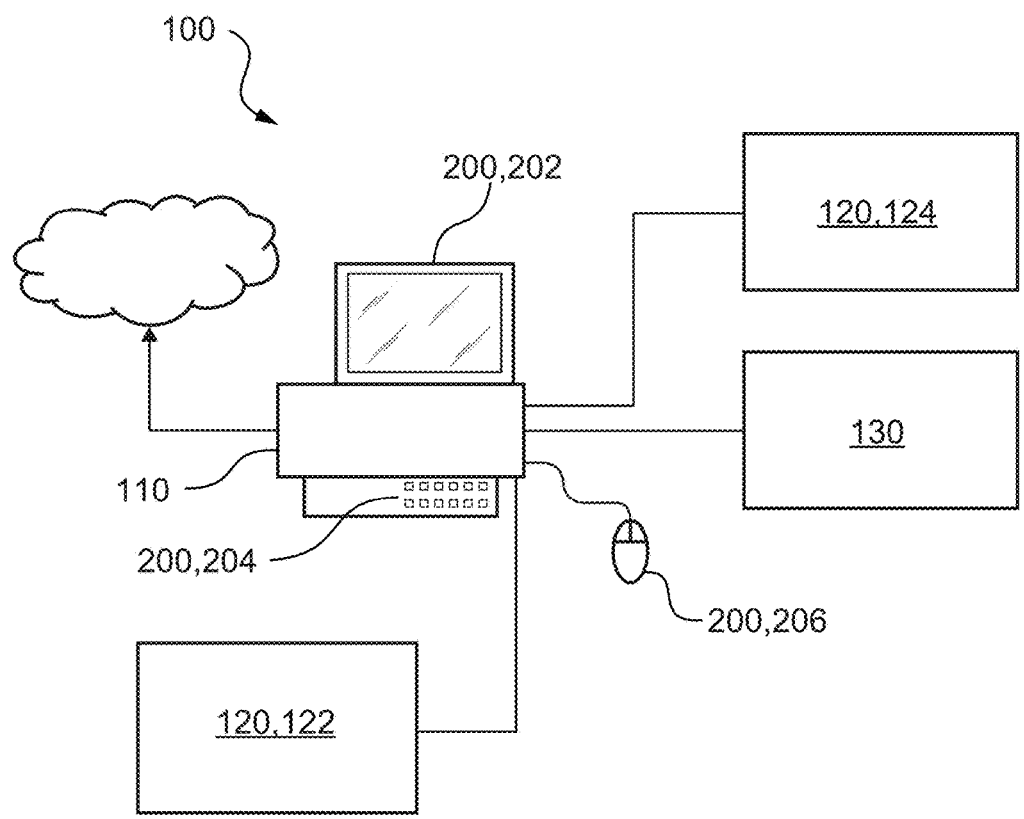
FIG. 5 is a system for determining an orthodontic treatment, according to certain embodiments of the present technology.

Accordingly, one embodiment of a system 100, suitable for implementing non-limiting aspects and embodiments of the present technology, is shown in FIG. 5.

It is to be expressly understood that the system 100 as depicted is merely an illustrative implementation of the present technology. Thus, the description thereof that follows is intended to be only a description of illustrative examples of the present technology. This description is not intended to define the scope or set forth the bounds of the present technology. In some cases, what are believed to be helpful examples of modifications to the system 100 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 100 may provide in certain instances simple implementations of the present technology, and that where such is the case they have been presented in this manner as an aid to understanding. As persons skilled in the art would understand, various implementations of the present technology may be of a greater complexity.

The system 100 of FIG. 5 comprises a computer system 110 for determining an orthodontic treatment for a patient. The computer system 110 is arranged to receive image data of the teeth 16 of the patient and to implement aspects and embodiments of a method 300 to determine the orthodontic treatment.

In this respect, in certain embodiments, the computer system 110 is operatively coupled to at least one imaging device 120 which is arranged to provide the image data to the computer system 110. In certain embodiments, the image data can be provided to the computer system 110 in a different way, such as via a storage device (not shown) or via a communication network (not shown). In certain embodiments, the system 100 also comprises an orthodontic appliance manufacture apparatus 130 for making at least a portion of the orthodontic appliance 10 suitable for the orthodontic treatment as determined by embodiments of the present method 300 and system 100.

In certain embodiments, the computer system 110 is connectable to the imaging device 120 and/or the orthodontic manufacture apparatus 130 via a communication network (not depicted). In some embodiments, the communication network is the Internet and/or an Intranet. Multiple embodiments of the communication network may be envisioned and will become apparent to the person skilled in the art of the present technology.

Figure 6:
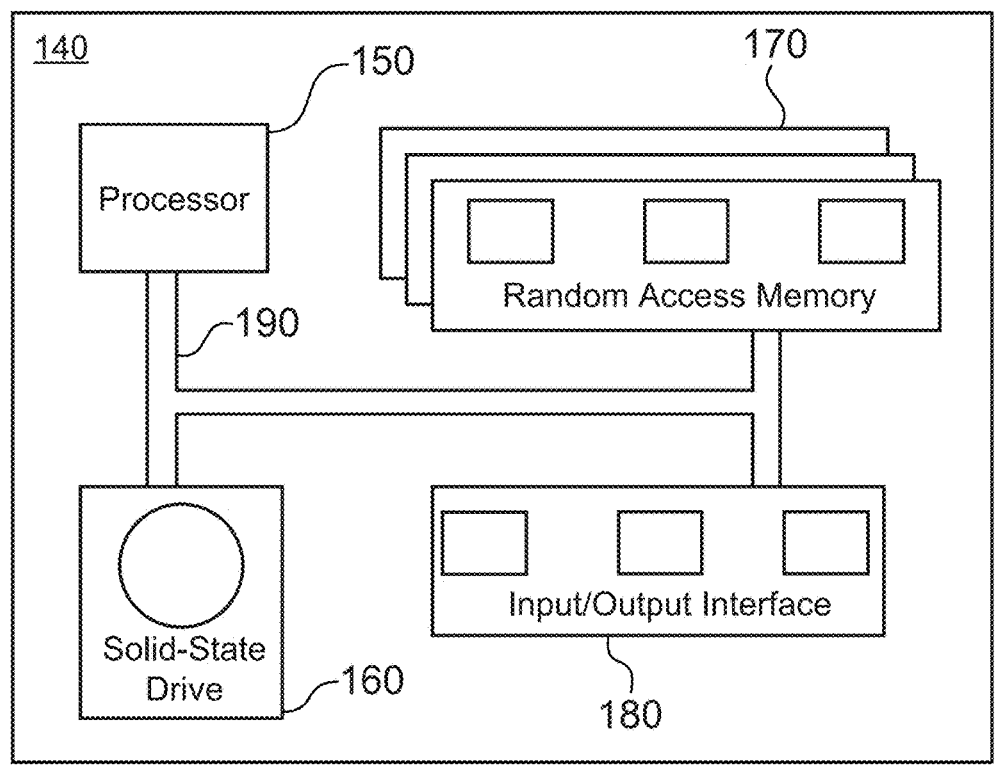
FIG. 6 is a computing environment of the system of FIG. 5, according to certain embodiments of the present technology.

Turning now to FIG. 6, certain embodiments of the computer system 110 have a computing environment 140 as illustrated schematically in FIG. 6. The computing environment comprises various hardware components including one or more single or multi-core processors collectively represented by a processor 150, a solid-state drive 160, a random access memory 170 and an input/output interface 180. Communication between the various components of the computing environment 140 may be enabled by one or more internal and/or external buses 190 (e.g. a PCI bus, universal serial bus, IEEE 1394 "Firewire" bus, SCSI bus, Serial-ATA bus, ARINC bus, etc.), to which the various hardware components are electronically coupled.

The random access memory 170 is configured in any known manner and arranged to store one or more of: set-up data, patient data, patient medical records of one or more patients, tooth image data of the one or more of the patients, and orthodontic appliance 10 data. The orthodontic appliance data comprises, for example, material properties (e.g. composition, elastic modulus, yield strength and spring back values) for different archwire materials (e.g. nickel-titanium (thermally activated, super-elastic), beta-titanium, cobalt-chromium-nickel, austenitic stainless steel, precious metal alloys (e.g. gold, silver, platinum alloys), polymer (nylon with silicon dioxide core and silicon resin middle layer, polyphenylene, methacrylates), polymer-coated) and for different archwire shapes (e.g. cross-sectional shape which is round, square, rectangular, multi-stranded, triangular, supercable) and different archwire diameters (e.g. diameters of 0.4 mm to 40.0 mm). Other data relating to any type of orthodontic appliance 10 which can affect the force applied by the orthodontic appliance on the tooth can also be included in the random access memory 170.

The input/output interface 180 allows enabling networking capabilities such as wire or wireless access. As an example, the input/output interface 180 comprises a networking interface such as, but not limited to, a network port, a network socket, a network interface controller and the like. Multiple examples of how the networking interface may be implemented will become apparent to the person skilled in the art of the present technology. For example, but without being limiting, the networking interface 180 may implement specific physical layer and data link layer standard such as Ethernet™, Fibre Channel, Wi-Fi™ or Token Ring. The specific physical layer and the data link layer may provide a base for a full network protocol stack, allowing communication among small groups of computers on the same local area network (LAN) and large-scale network communications through routable protocols, such as Internet Protocol (IP).

According to implementations of the present technology, the solid-state drive 160 stores program instructions suitable for being loaded into the random access memory 170 and executed by the processor 150 for executing methods 300 according to certain aspects and embodiments of the present technology. For example, the program instructions may be part of a library or an application.

In this embodiment, the computing environment 140 is implemented in a generic computer system which is a conventional computer (i.e. an "off the shelf" generic computer system). The generic computer system is a desktop computer/personal computer, but may also be any other type of electronic device such as, but not limited to, a laptop, a mobile device, a smart phone, a tablet device, or a server.

In other embodiments, the computing environment 140 is implemented in a device specifically dedicated to the implementation of the present technology. For example, the computing environment 140 is implemented in an electronic device such as, but not limited to, a desktop computer/personal computer, a laptop, a mobile device, a smart phone, a tablet device, a server, specifically designed for determining the orthodontic treatment. The electronic device may also be dedicated to operating other devices, such as the imaging device 120 or the orthodontic manufacture 130 apparatus for making the orthodontic appliance 10.

In some embodiments, the computer system 110 is connected to the imaging device 120 and/or the orthodontic manufacture apparatus 130. In some alternative embodiments, the computer system 110 or the computing environment 140 is implemented, at least partially, on the imaging device 120 and/or the orthodontic manufacture apparatus 130. In some alternative embodiments, the computer system 110 may be hosted, at least partially, on a server. In some alternative embodiments, the computer system 110 may be partially or totally virtualized through a cloud architecture.

Referring back to FIG. 5, the computer system 110 has at least one interface device 200 for providing an input or an output to a user of the system 100. In the embodiment of FIG. 5, the interface device is a screen 202 for providing a visual output to the user of the system 100, the visual output being the determined orthodontic treatment for example. In other embodiments, the interface device 200 may be a monitor, a speaker, a printer or any other device for providing an output in any form such as image-form, written form, printed form, verbal form, 3D model form, or the like.

In the embodiment of FIG. 5, the interface device 200 also comprises a keyboard 204 and a mouse 206 for receiving input from the user of the system 100. Other interface devices 200 for providing an input to the computer system 110 can include, without limitation, a USB port, a microphone, a camera or the like.

The computer system 110 may be connected to other users, such as through their respective clinics, through a server (not depicted). The computer system 110 may also be connected to appointment management software which could schedule appointments or follow-ups based on the determination of the orthodontic treatment by embodiments of the present system 100 and method 300.

In some embodiments, the computing environment 140 is distributed amongst multiple systems, such as the imaging device 120, the orthodontic apparatus 130, and/or the server.

In some embodiments, the computing environment 140 may be at least partially implemented in another system, as a sub-system for example. In some embodiments, the computer system 110 and the computing environment 140 may be geographically distributed.

As persons skilled in the art of the present technology may appreciate, multiple variations as to how the computing environment 140 is implemented may be envisioned without departing from the scope of the present technology.

Turning now to the imaging device 120 shown in FIG. 5, any device which can capture and/or process images of the teeth 16 and/or surrounding tissues 28 of the patient can be used. In certain embodiments, the images comprise one or more of: images of the crown portion 24 (external), images of the crown portion 24 (internal), images of the root portion 26 (external), images of the root portion 26 (internal), images of the surrounding tissues 28, images of the nerve pathways in the teeth 16 and in the surrounding soft tissue, images of the bone near the teeth 16, and images of the oral region. The images can be two-dimensional or three-dimensional.

In certain embodiments, the images are one or more of: computed tomography (CT) images, x-ray images, digitalized three-dimensional physical model images, magnetic resonance images, nuclear medicine images, photographic images, and the like. Any type of image format visualizing the tooth and/or the surrounding areas is acceptable within the context of the present technology.

In certain embodiments, the imaging device 120 is an intra-oral scanner 122 providing three-dimensional digital models of the teeth 16. Intra-oral scanners 122 typically have a component which can be received in the oral region and having a light source for providing light to the oral region requiring imaging and an imaging sensor for capturing images of the oral region. A computer system component of the intra-oral scanner can receive the captured images and create digital 3D surface models (e.g. a "mesh") of the oral region. This technique provides an alternative to making traditional plaster models of the oral region followed by their digital imaging.

In certain embodiments, the imaging device 120 is a computed tomography (CT) scanner 124 providing CT scan images. CT scan images are three-dimensional images of providing x-ray level detail of the teeth, soft tissues, nerve pathways and bone. Different types of CT scanners can provide panoramic, cephalometric or cone beam projections.

In certain embodiments, the imaging device 120 is one or more of an x-ray apparatus providing x-ray two-dimensional x-ray images of the oral region, a magnetic resonance imaging device providing magnetic resonance images, and an ultrasound apparatus for providing ultrasound images of the oral region. In any of the embodiments of the imaging device 120, the imaging device may comprise an imaging device processor for storing the images and optionally for processing the images.

In the embodiment illustrated in FIG. 5, the imaging device 120 comprises two imaging devices 120: the intra-oral scanner 122 and the CT scanner 124. In this case, the intra-oral scanner 122 provides 3D surface models with information on surfaces of the teeth and/or surrounding tissues, whereas the CT scanner 124 provides 3D images of the teeth, roots, bone, soft tissue and nerve pathways. The images thus obtained are complementary and provide surface information about the tooth such as its topography, as well as tooth/bone/gum internal structure information.

Figure 7:
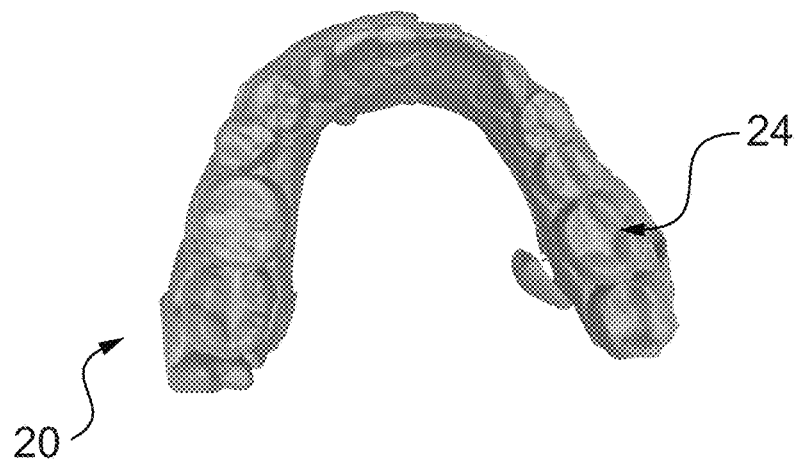
FIG. 7 is a 3D image of a crown portion and surrounding tissues of a patient obtained using an intra-oral scanner.

FIG. 7 shows a 3D image (external) of the crown portion 24 and surrounding tissues 28 of a patient obtained using the intra-oral scanner 122 according to certain embodiments of the present technology. In this embodiment, the intra-oral scanner 122 was of a type providing images in STL and/or OBJ format. Any other image format is also included within the scope of the present technology.

Figure 8:
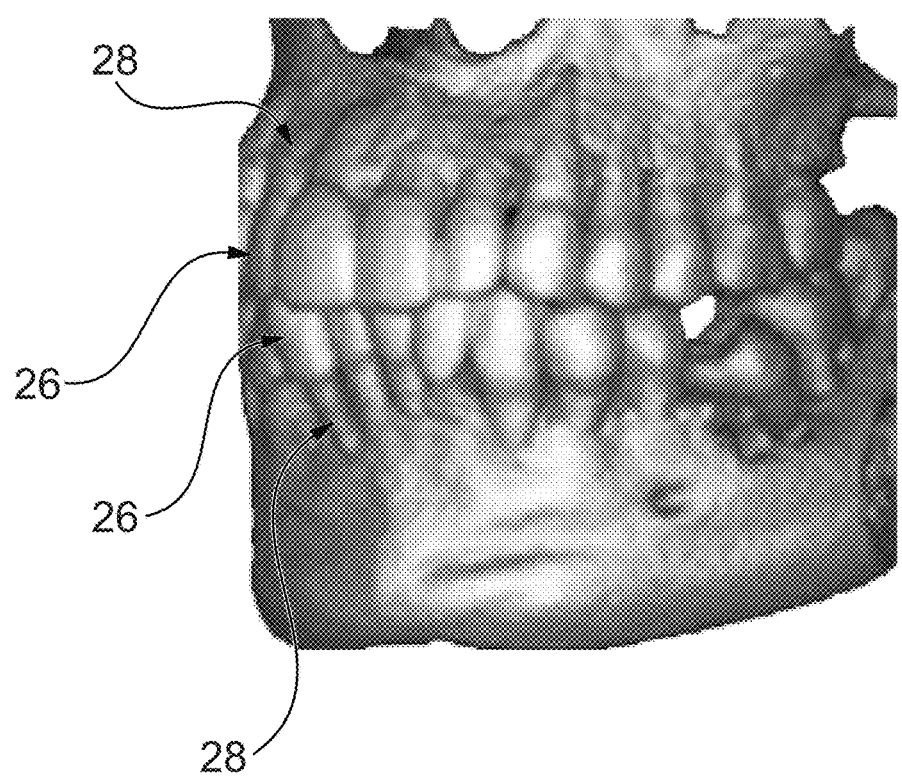
FIG. 8 a CT image of a jaw of a patient showing the crown portion and root portion of each tooth obtained by a CT scanner.

FIG. 8 shows a CT image of the jaw of a patient, showing the crown portion 24 and root portion 26 of each tooth, obtained by the CT scanner 124 according to certain embodiments of the present technology. In this embodiment, the CT scanner 124 was of a type providing images in DiCOM format. It will be appreciated that the image data of the patient's teeth 16 and surrounding tissues 28 could be obtained by any other means and in any other format.

Turning now to the orthodontic manufacture apparatus 130 of the system 100 of FIG. 5. In certain embodiments, the system 100 optionally includes the orthodontic manufacture apparatus 130. The orthodontic manufacture apparatus 130 comprises any apparatus suitable for making the orthodontic appliance 10 such as the bracket 12, the archwire 14, an orthodontic trainer (not shown), an orthodontic retainer (not shown), a mouthguard, or any other type of orthodontic appliance 10.

Orthodontic manufacture apparatus 130 for making brackets 12 include, for example, casting apparatus, moulding apparatus, 3D printing apparatus, or the like. Orthodontic manufacture apparatus 130 for making archwires 14 include robotic bending apparatus, heating/cooling apparatus, smart material manufacturing apparatus, and the like. Orthodontic manufacture apparatus 130 for making trainers, retainers or mouthguards include thermoforming apparatus, moulding apparatus, 3D printing apparatus and the like. One such orthodontic manufacture apparatus 130 suitable for the manufacture of orthodontic archwires is described in U.S. Ser. No. 16/014,253 filed on Jun. 21, 2018, the contents of which are incorporated herein.

Figure 9:
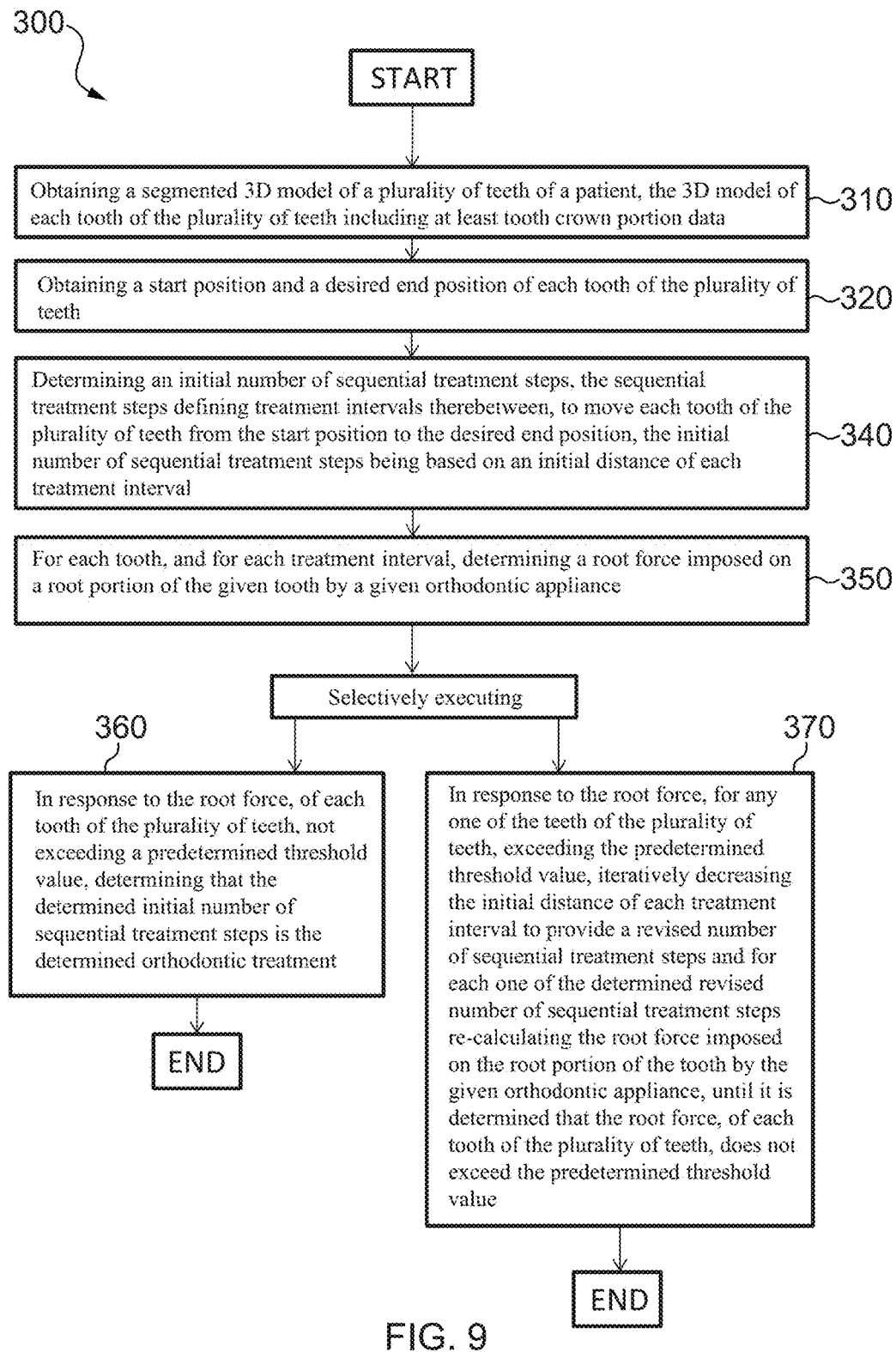
FIG. 9 is a diagram of a method for determining an orthodontic treatment, according to certain embodiments of the present technology.

With reference now to FIG. 9, in certain embodiments the computer system 110 is configured to execute the method 300 for determining the orthodontic treatment. More specifically, the method 300 is configured to determine the number of sequential steps in the orthodontic treatment. The method 300 will now be described in further detail below.

STEP 310: obtaining a segmented 3D model of a plurality of teeth of a patient, the segmented 3D model of each tooth of the plurality of teeth including at least tooth crown portion data The method 300 starts at step 310 with the computer system 110 obtaining a segmented 3D model of the plurality of teeth 16 of the patient. By segmented 3D model of a plurality of teeth 16 is meant a 3D image of the plurality of teeth 16, in which each tooth 16 of the plurality of teeth 16 has been digitally separated from the other teeth of the plurality of teeth such that each tooth can be individually digitally manipulated. The 3D image includes at least the crown portion 24 of the plurality of teeth 16.

In certain embodiments, the segmented 3D model of the plurality of teeth includes only the crown portion 24 of the teeth 16 and does not include the root portion 26 of the plurality of teeth 16 nor the surrounding tissues 28. In such cases, the segmented 3D model of the plurality of teeth 16 is derived from 3D images of external portions of the teeth 16, such as those obtained from the intra-oral scanner 122.

In certain embodiments, the segmented 3D model of the plurality of teeth 16 includes the crown portion 24 and the root portion 26 of the teeth 16, and may or may not also include the surrounding tissues 28. In this case, the segmented 3D model may be obtained by combining 3D surface images of the crown portion 24 obtained by one type of imaging device 120 (e.g. the intra-oral scanner 122), and images of the root portions 26 of the teeth 16 obtained by the same or another type of imaging device 120 (e.g. CT scanner).

In certain embodiments, the segmented 3D model of the plurality of teeth 16 is obtained in a set-up stage (not shown) before step 310. In certain embodiments, the segmented 3D model of the teeth 16 is obtained from the imaging device(s) 120 themselves, the imaging device(s) 120 having captured the images of the teeth 16 (e.g. 3D optical image data), and digitally parsed the 3D optical image data to digitally separate each tooth 16 of the plurality of teeth 16 to create the segmented 3D model.

Figure 10:
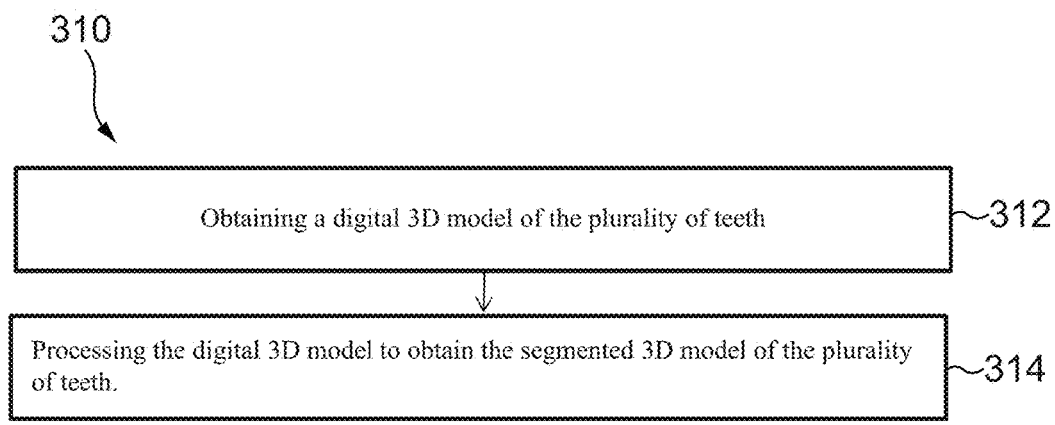
FIG. 10 is a diagram of certain steps of the method of FIG. 9, according to certain embodiments of the present technology.

In certain other embodiments, the image segmentation is performed by the computer system 110 having obtained the image data from the imaging device(s) 120. In such cases, the method step 310 is illustrated in FIG. 10 and comprises step 312 of obtaining the digital 3D model of the plurality of teeth 16, and step 314 of processing the digital 3D model to obtain the segmented 3D model of the plurality of teeth 16. In step 312, obtaining the digital 3D model comprises obtaining 3D optical image data of the plurality of teeth 16, such as from the intra-oral scanner 122. In Step 314, processing the digital 3D model to obtain the segmented 3D model of the plurality of teeth 16 comprises digitally separating each tooth of the plurality of teeth in the 3D optical image data to obtain the segmented 3D image data of the plurality of teeth 16.

Figures 11A, 11B, 11C:
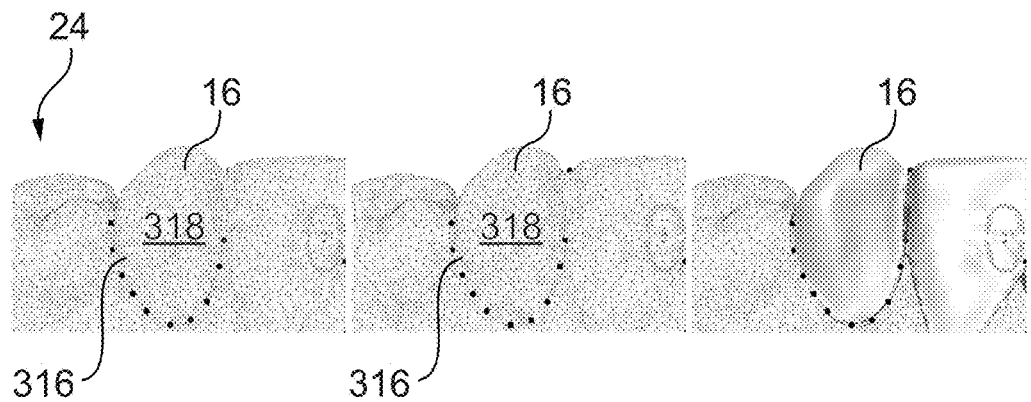
FIGS. 11a, 11b and 11c illustrate a method of obtaining a segmented 3D model of the teeth, according to certain embodiments of the present technology.

As best seen in FIG. 11a-11c, the processing step 314 for parsing of the 3D image data (which as illustrated includes only images of the crown portions 24 and the surrounding tissues 28) comprises identifying a boundary 316 of each tooth 16 using a contour 318 of the tooth 16. In the illustrated embodiment, at least a part of the boundary 316 of each tooth 16 is along the gum-line, and between two adjacent teeth 16. This is performed for each tooth 16 of the plurality of teeth 16.

In certain embodiments, image recognition software is used to parse the 3D image data. The 3D image data is processed as "slices" across the tooth root portion 26. The slicing is performed one or more of: proximally from a distal end of the root portion 26 towards the crown portion 24, and distally from a proximal end of the crown portion 24 towards the root portion 26. Using image recognition software, the gum line is detected and a removeable marker positioned.

STEP 320: Obtaining a start position and a desired end position of each tooth of the plurality of teeth The method continues at step 320 by obtaining a start position and a desired end position of each tooth 16 of the plurality of teeth 16. By start position is meant the location of each tooth 16 at or before the commencement of the orthodontic treatment. By desired end position is meant the location of each tooth 16 at or after the conclusion of the orthodontic treatment. The tooth location may be defined in any convenient manner, such as for example in terms of a position relative to the patient's mouth, relative to another tooth, relative to another reference point, or in terms of a translation/rotation movement (e.g. 1 mm towards the middle of the jaw and an anticlockwise rotation of 2°).

Figure 12:
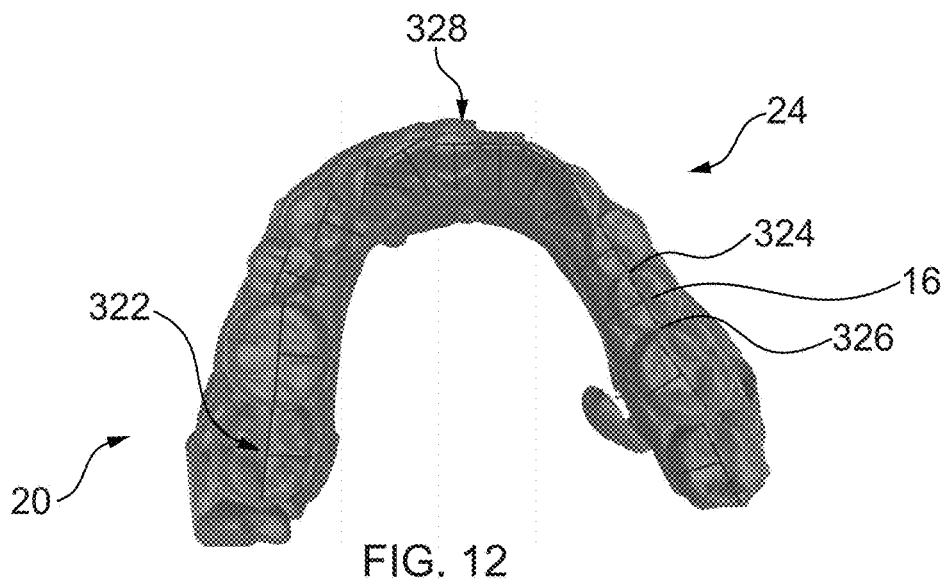
FIG. 12 illustrates the 3D image of FIG. 7 and including an identifier for each tooth, according to certain embodiments of the present technology.

In the embodiment illustrated in FIG. 12, for obtaining the start position, each tooth 16 is individually identified in terms of its relative size and position in the mouth using an identifier 322. The identifier 322 for each tooth 16 is a mesiodistal marker 322. The mesiodistal marker 322 is a line, along a two-dimensional plane, joining the mesial and distal surfaces 324, 326 of each tooth 16. The mesial surface 324 of the tooth 16 is the surface that is closer to the middle or front 328 of the jaw. The distal surface 326 of the tooth 16 is the surface that is further from the middle or front 328 of the jaw. The mesiodistal marker 322 also includes a direction marker 330, perpendicular to the mesiodistal marker 322 and extending from a mid-point along the mesiodistal marker. In this way, the mesiodistal marker 3222 for each tooth 16 provides information about the size of each tooth 16 and its orientation.

Figure 13:
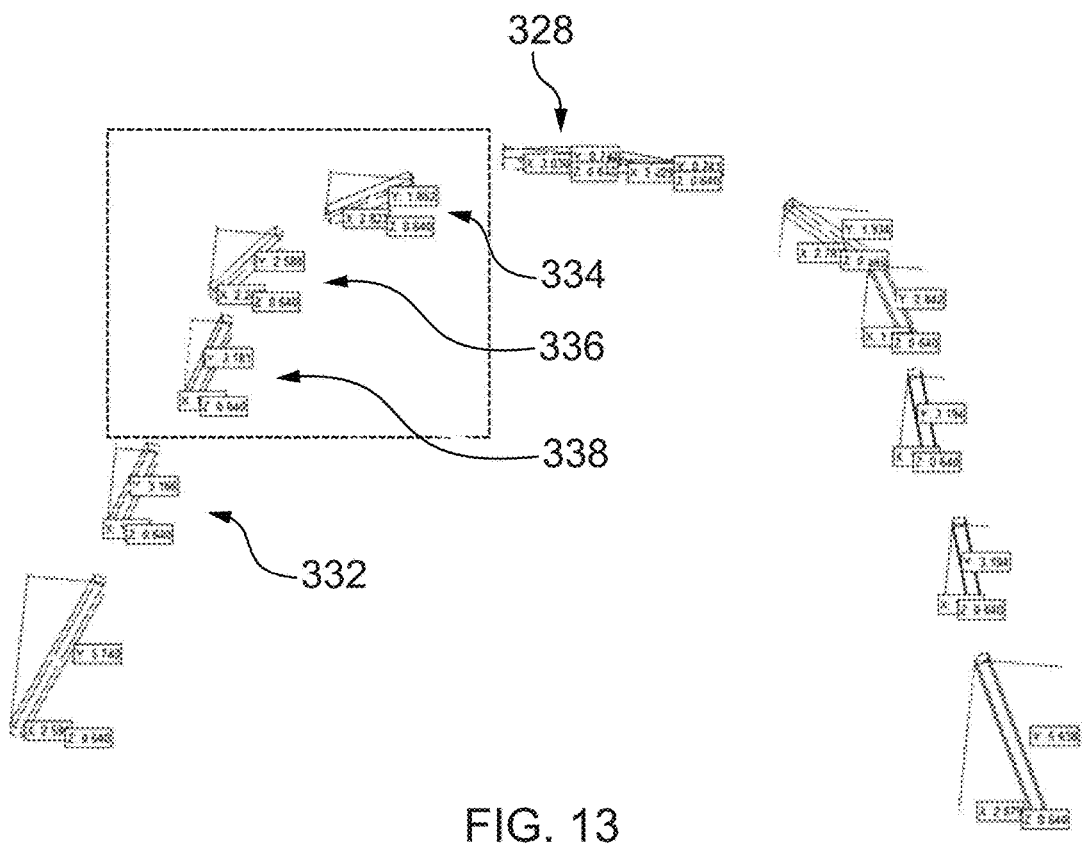
FIG. 13 illustrates the teeth of FIG. 7 and FIG. 13 denoted as x-y-z coordinates, according to certain embodiments of the present technology.

Each tooth is also allocated an x-y-z co-ordinate 332 identifying its position and optionally size (FIG. 13). The z-axis is the same for all teeth 16.

It will be appreciated that the mesiodistal marker 322 and the x-y-z co-ordinate 332 for each tooth 16 can be determined before, during or after obtaining the segmented 3D model.

The desired end position for each tooth 16 can be determined in a number of ways. It may be determined manually, automatically or with a combination of manual and automatic methods. In embodiments where the desired end position is determined manually, the user of the system 100, such as the clinician, identifies, for each tooth 16, the desired end position, using for example the interface device such as the mouse 206, the keyboard 204 or a touchscreen (not shown). Manual determination may also comprise manipulation of a physical model, followed by its digitalization.

In embodiments where the desired end position is determined automatically, the computer system 110 is arranged to determine end positions for each tooth 16 based on template archforms (shape and/or contour of the dental arch and including rotational orientation of each tooth), stored in a database such as the random access memory 170. In these cases, the computer system 110 identifies a closest desired archform template based on the patient's current archform, and then determines, for each tooth, translational/rotational movement required to achieve the position and orientation of each of the patient's teeth 16 to the template archform.

In embodiments where the desired end position is determined semi-automatically, the computer system 110 provides a number of suggested end positions for each tooth, again based for example on template archforms, from which the user of the system 100 selects the desired end position.

Figure 14:
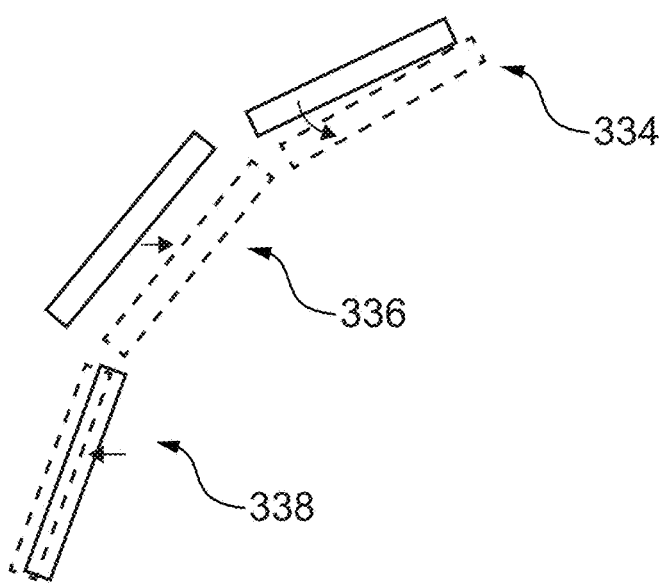
FIG. 14 is a schematic illustration of some of the teeth of FIG. 7, 12 or 13 showing a starting position and a desired end position, according to certain embodiments of the present technology.

Depending on the start position of the tooth 16, the movement of the tooth 16 from the start position to the desired end position may be one or more of a translational (linear) movement, a rotational movement, or a maintaining of position. To illustrate this, FIG. 14 shows an enlarged view of three of the teeth 16 of FIG. 13: a lower left lateral tooth 334, a lower left cuspid tooth 336 and a lower left first bicuspid tooth 338. The starting positions of these three teeth 334, 336, 338 are shown as a solid line. The desired end positions of each of these three teeth 334, 336, 338 are shown in dotted line. As can be seen, to be positioned in the desired end position, the lower left lateral tooth 334 will need to be moved laterally and rotationally, the lower left cuspid tooth 336 will need to be moved linearly towards the middle 328 of the jaw, and the lower left first bicuspid 338 will need to be moved linearly away from the middle 328 of the jaw.

STEP 340: determining an initial number of sequential treatment steps to move each tooth of the plurality of teeth from the start position to the desired end position, the initial number of sequential treatment steps being based on an initial distance of each treatment interval At Step 340 of the method 300, an initial number of sequential treatment steps 342 to move each tooth 16 of the plurality of teeth from the start position to the desired end position is determined. The initial number of sequential treatment steps 342 define treatment intervals 344 therebetween. The initial number of sequential treatment steps 342 is determined based on an initial distance 346 of each treatment interval 344.

Figure 15:
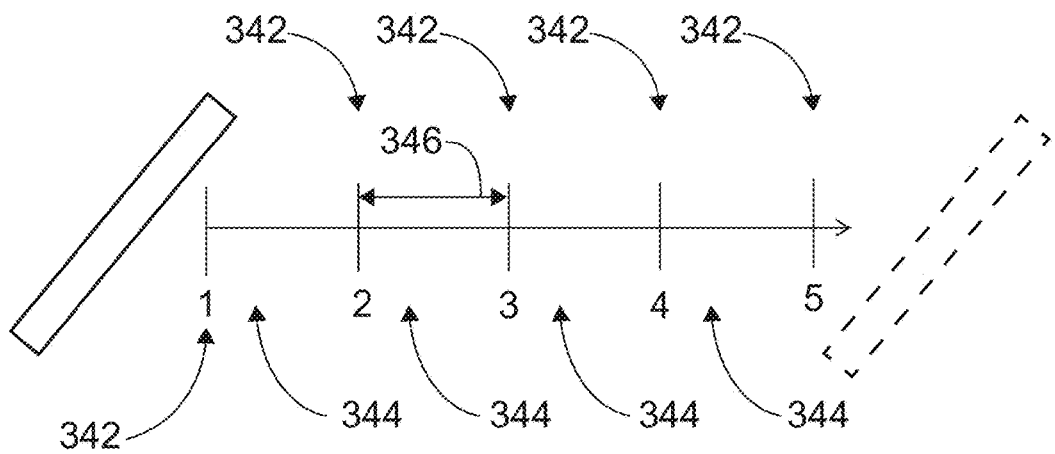
FIG. 15 is a schematic illustration of the starting position and desired end position of one tooth and including sequential treatment steps therebetween, according to certain embodiments of the present technology.

FIG. 15 illustrates step 340 schematically, in which based on an initial distance 346 of 200 microns per treatment interval 344, five initial treatment steps 342 have been determined, in order to move the tooth 16 a total linear distance of one millimeter.

The method 300 assumes that each treatment interval 344 has the same distance, although variable distances within each treatment interval 344 are also possible. The initial distance 346 is an initial maximum permitted distance of movement of each tooth 16 during each treatment interval 344. The initial distance 346 is preferably predetermined. In one embodiment, the initial distance 346 of the treatment interval 344 is a translational (linear) movement of 200 microns. In other embodiments, the initial distance 346 may be higher or lower depending on various factors such as one or more of: the type of tooth 16 being treated, an age group of the patient being treated, a property of the bone of the patient being treated, etc.

As mentioned above, the sequential treatment steps 342 can signify a change in a force being applied to the teeth 16, such as through a change in a property of the orthodontic appliance 10 being applied to the teeth 16 such as archwire 14 thickness, archwire 14 bend angle, archwire 14 material etc.

STEP 350: for each tooth of the plurality of teeth, and for each treatment interval, determining a root force imposed on a root portion of the given tooth by the given orthodontic appliance The method 300 comprises, in Step 350, for each tooth 16 of the plurality of teeth 16 and for each treatment interval 344, determining a root force imposed on periodontal ligaments 32 around the root portion 26 of the given tooth 16 by a given orthodontic appliance 10. In certain embodiments, the root force comprises an average force imposed on periodontal ligaments around an entirety of the tooth root portion.

Figure 16:
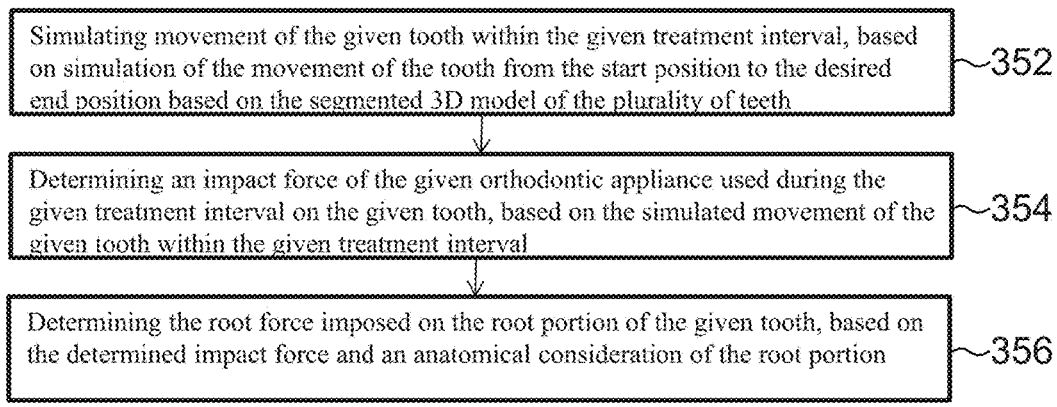
FIG. 16 is a diagram of certain steps of the method of FIG. 9, according to certain embodiments of the present technology.

In certain embodiments, the determination of the force around the root portion 26 is carried out as defined in steps 352, 354 and 356 (FIG. 16).

In step 352, the method 300 comprises simulating movement of the given tooth 16 within the given treatment interval 344, based on simulation of the movement of the given tooth 16 from the start position to the desired end position based on the segmented 3D model of the plurality of teeth 16.

In step 354, the method 300 comprises determining an impact force of the given orthodontic appliance 10 used during the given treatment interval 344 on the given tooth 16. This is based, at least in part, on the simulated movement of the given tooth 16 within the given treatment interval 344, as determined in Step 352. In this respect, the method 300 also includes obtaining an input of at least one parameter of the orthodontic appliance 10 which can affect a force applied by the orthodontic appliance 10, such as but not limited to, a type of archwire 14 material, the archwire 14 diameter, the archwire 14 bend angle, a method of forming the archwire 14 etc. The information can be retrieved from a database, such as those stored in the random access memory 170, or from any other source. In certain embodiments, the input is provided by the user of the system, for example, at method step 310 or during the set-up step. The input on the orthodontic appliance 10 can be selected by the user of the system 100, such as by means of a drop-down list presented on the screen 202.

In Step 354, the determining the impact force on the given tooth is based on creating a model of the interaction of the teeth with the orthodontic appliance 10 or any other orthodontic appliance, such as a mouthguard, a bite plane, a transpalatal bar, lingual arches or the like. In certain embodiments, the model is based on modelling the orthodontic appliance 10 around the plurality of teeth 16, in which boundary conditions are imposed which reflect the deformation of the orthodontic appliance 10 caused by the contact of the orthodontic appliance 10 with the teeth 16. The internal stresses in the orthodontic appliance 10 caused by the contact of the orthodontic appliance 10 with the teeth 16 is taken into account. In certain embodiments, Step 354 is performed through a Finite Element Method (FEM) based on an interaction of the plurality of teeth 16 and the orthodontic appliance.

In Step 356, the root force imposed on the root portion of the given tooth 16 is determined based on the determined impact force of the given tooth 16 and an anatomical consideration of the root portion 26 of the given tooth 16. For example, information regarding the size and shape of the root portion 26 may be obtained in any of the preceding or current steps of the method 300, and used in Step 356. In certain embodiments, the root portion anatomical information is obtained from CT scan data. In this respect, the method 300 further comprises obtaining CT scan data of the plurality of teeth 16, such as from the CT scanner 124, segmenting the CT scan data to obtain individually manipulateable data of each tooth, and parsing the segmented CT scan data into crown portion 24 data and root portion 26 data. In certain embodiments, the determining the root force imposed on the root portion 26 takes into account at least one of: root portion topography, root portion geometry, root portion length, root portion surface area, crown portion topography, and type of tooth.

In certain embodiments, the model of the interaction of the teeth with the orthodontic appliance 10 is as proposed by Gilbert Dudley Fish in "Technology in Orthodontics" *International Journal of Orthodontia*, June 1917, 3: 324-341 (which is incorporated herein in its entirety). Namely, the tooth is assumed to be a solid body partially immersed in a linear elastic medium (periodontium) and having a stable equilibrium in the absence of load application on the tooth.

When load is applied, the relationship between the acting forces and the tooth displacement can be expressed as follows:

$$\begin{pmatrix} \vec{\rho} \\ \vec{\varphi} \end{pmatrix} = \begin{pmatrix} \hat{\alpha} & \hat{\gamma} \\ \hat{\gamma}^T & \hat{\beta} \end{pmatrix} \begin{pmatrix} \vec{F} \\ \vec{M} \end{pmatrix}$$

Where $\vec{\rho}$ is the movement of the pole, $\vec{\varphi}$ is the vector of small rotation of the tooth, $\hat{\alpha}$, $\hat{\beta}$, $\hat{\gamma}$ characterize the malleability (compliance) of the medium (periodontium), $\vec{F}$ is the main vector of power system, and $\vec{M}$ is the main point of the system of forces relative to the pole.

The optimization criterion is to minimize the difference between the planned initial movement o the tooth $\vec{u}^*(\vec{r})$ and one that can be provided in a particular situation $\vec{u}(\vec{r})$:

$$(\vec{u}^*(\vec{r}) - \vec{u}(\vec{r}))^2 \rightarrow \min, \vec{r} \in V,$$

$$\vec{u}*(\vec{r}) = \vec{\rho}* + \vec{\varphi}* \times \vec{r}, \vec{r} \in V,$$

Where V is the region occupied by the tooth root, $\vec{\rho}*$ is the planned pole displacement $\vec{\rho}* = \{x^*, y^*, z^*\}^T$, $\vec{\varphi}*$ is the vector of the planned small tooth rotation angle around the pole $\vec{\varphi}* = \{\varphi^*_x, \varphi^*_y, \varphi^*_z\}^T$.

The movement of any point of the tooth is determined by the ratio:

$$\vec{u}(\vec{r}) = \vec{\rho} + \vec{\varphi} \times \vec{r}.$$

The translational (gradual) movement of the tooth will occur in the direction of the force line in the event that the force vector is parallel to one of the main axes of the compliance matrix with the translational motion $\hat{K}$:

$$\hat{K} = (\hat{\alpha} - \hat{\gamma}\hat{\beta}^{-1}\hat{\gamma}^T).$$

The equations describing the behaviour of the elastic medium are as follows:

$$\vec{\nabla} \cdot \tilde{\sigma} = 0,$$

$$\tilde{\sigma} = \tilde{\tilde{C}} \cdot \tilde{\varepsilon},$$

$$\tilde{\varepsilon} = \tfrac{1}{2}\vec{\nabla}\vec{u} + \vec{\nabla}\vec{u}^T.$$

The boundary conditions are as follows:
1. The system of orthodontic forces is carried out thanks to a corrective structure that can be attached to the crown of the tooth $$\vec{F}|_{S_F} = \vec{F}.$$

2. The external border of the periodontium is considered to be fixed (this condition models the connection with the bone):

$$\vec{u}|_{S_C} = 0.$$

Figure 17:
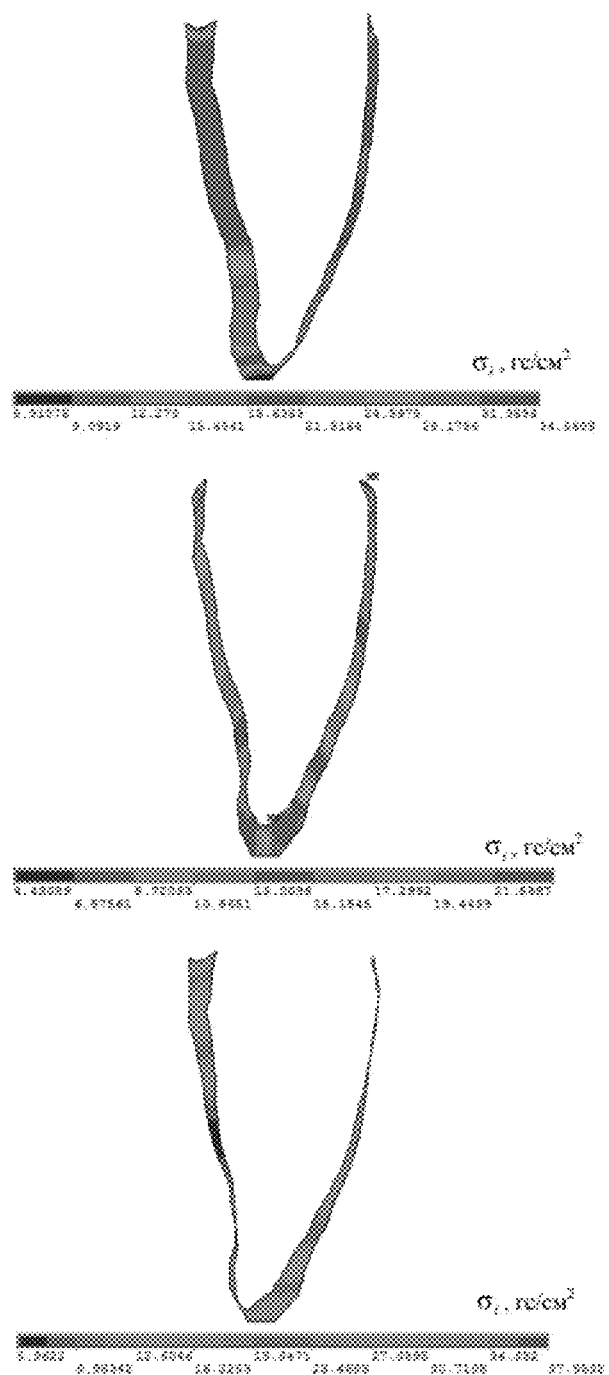
FIG. 17 shows stress distributions in the periodontium of a tooth undergoing a simulated treatment of diastema, extrusion and inclination (upper, middle and lower graphs, respectively), as determined according to certain embodiments of the present technology.

The relationship of force to tooth movement is described as "center of resistance". In certain embodiments, determined root force takes into account the type of orthodontic treatment being applied in terms of the applied forces. For example, determined root force for treatment of (a) diastema (a gap between teeth) is shown in FIG. 17 (top), (b) extrusion correction is shown in FIG. 17 (middle), and (c) inclination is shown in FIG. 17 (bottom).

STEP 360: Selectively executing, in response to the root force of each tooth of the plurality of teeth not exceeding a predetermined threshold value, determining that the determined initial number of sequential treatment steps is the determined orthodontic treatment At Step 360, the method 300 comprises selectively executing, in response to the root force not exceeding a predetermined threshold value, determining that the determined initial number of sequential treatment steps 342 is the determined orthodontic treatment. The method 300 ends at Step 360 if this condition is met.

The predetermined threshold value can be obtained from any suitable source, such as look-up tables, experimental data, etc. The predetermined threshold value may be different for the different teeth of the plurality of teeth 16. For example, the predetermined threshold value may vary based on the movement being imposed on the tooth, the type of tooth, the shape of the tooth, the quality of the bone of the patient, the age of the patient, and other physiological and anatomical factors relating to one or both of the patient or the patient's teeth.

STEP 370: In response to the root force for any one of the teeth of the plurality of teeth exceeding the predetermined threshold value, iteratively decreasing the initial distance of each treatment interval to provide a revised number of sequential treatment steps and for each one of the determined revised number of sequential treatment steps re-calculating the root force imposed on the root portion of the tooth by the given orthodontic appliance, until it is determined that the root force, of each tooth of the plurality of teeth, does not exceed the predetermined threshold value Step 370 comprises, in response to the root force exceeding the predetermined threshold value, iteratively decreasing the initial distance 346 to provide a revised number of sequential treatment steps 371 and for each one of the determined revised number of sequential treatment steps 371, re-calculating the root force imposed on the root portion 26 of the tooth 16 by the given orthodontic appliance 10, until it is determined that the root force, of each tooth 16 of the plurality of teeth 16, does not exceed the predetermined threshold value. The revised number of sequential treatment steps 371 which gave rise to the root force, of each tooth 16 of the plurality of teeth 16, not exceeding the predetermined threshold value is determined to be the determined orthodontic treatment.

In certain embodiments, the decreasing the initial distance 346 comprises decreasing the initial distance 346 by an amount proportional to an excess amount of the root force above the predetermined threshold. In other embodiments, the initial distance 346 can be incrementally decreased according to predetermined values, or values provided by the user.

Figure 18:
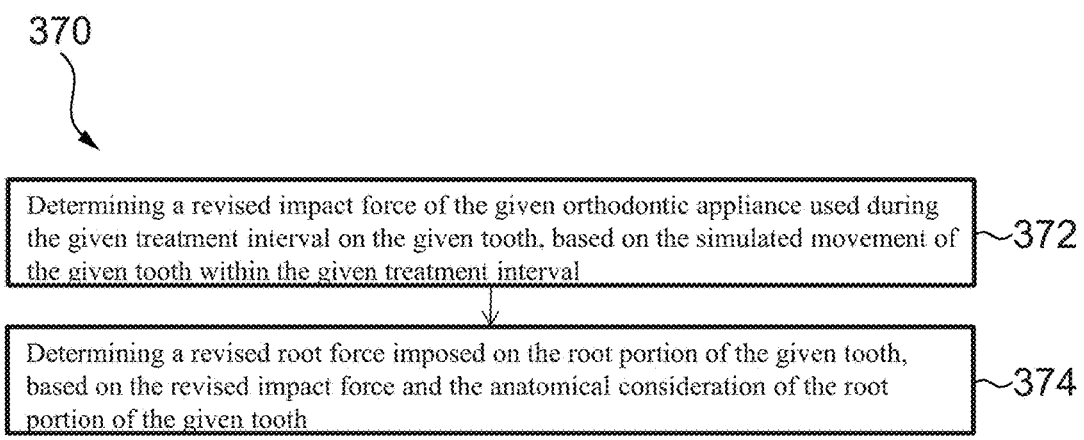
FIG. 18 is a diagram of certain steps of the method of FIG. 9, according to certain embodiments of the present technology.

In certain embodiments, the force imposed on the root portion 26 of the tooth 16 by the given orthodontic appliance 10 is recalculated according to Steps 372 and 374 (FIG. 18).

In Step 372, the method 300 comprises determining a revised impact force of the given orthodontic appliance 10 used during the given treatment interval 344 on the given tooth 16, based on the simulated movement of the given tooth 16 within the given treatment interval 344. The simulation from Step 352 can be used here, or the simulation determined again.

In Step 374, the method comprises determining a revised root force imposed on the root portion 26 of the given tooth 16, based on the revised impact force and the anatomical consideration of the root portion 26 of the given tooth 16. The anatomical consideration in Step 374 is the same as the anatomical consideration in Step 356.

In Step 380, the method 300 comprises displaying the determined orthodontic treatment on the interface device 200, such as the screen 202, as an output. Other outputs are possible such as a recommendation of an alternative orthodontic appliance 10 based on the determined impact force and/or root force. For example, based on a determined impact force, a recommendation may be made to use a retainer as well as brackets and archwire as an orthodontic appliance 10.

Step 380: determining intermediate collisions between adjacent teeth in the plurality of teeth for each treatment interval between each sequential treatment step of the initial number of sequential steps, the determining intermediate collisions being based on the determined simulated movement of each tooth In an optional Step 380, during or after the simulation Step 352, the method comprises determining intermediate collisions between adjacent teeth 16 in the plurality of teeth 16 for each treatment interval 344 between each sequential treatment step of the initial number of sequential steps 342, the determining intermediate collisions being based on the determined simulated movement of each tooth. The intermediate collisions are determined on the basis of the segmented 3D models of the teeth, including at least the crown portion 24 data. In certain embodiments, the determination of the intermediate collisions uses binary trees of bounding volumes. In certain embodiments, if a collision is detected, the method comprises instructing the computer system 110 to send an alert to the user, such as by displaying on the screen 202, or the like. In other embodiments, if a collision is detected in any treatment interval, the method comprises adapting the initial number of treatment steps 342 or recommending adaptation of the orthodontic appliance.

It should be expressly understood that not all technical effects mentioned herein need to be enjoyed in each and every embodiment of the present technology.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A method for determining an orthodontic treatment having a number of sequential treatment steps with a given orthodontic appliance, the sequential treatment steps defining treatment intervals therebetween, the method executable by a processor of a computer system, the method comprising:
   obtaining a segmented 3D model of a plurality of teeth of a patient, the segmented 3D model of each tooth of the plurality of teeth including at least crown portion data;
   obtaining a start position and a desired end position of each tooth of the plurality of teeth;
   determining an initial number of sequential treatment steps to move each tooth of the plurality of teeth from the start position to the desired end position, the initial number of sequential treatment steps being based on an initial distance of each treatment interval;
   for each tooth of the plurality of teeth, and for each treatment interval, determining a root force imposed on a root portion of the given tooth by the given orthodontic appliance;
   selectively executing:
      in response to the root force of each tooth of the plurality of teeth not exceeding a predetermined threshold value, determining that the determined initial number of sequential treatment steps is the determined orthodontic treatment; and
      in response to the root force, for any one of the teeth of the plurality of teeth, exceeding the predetermined threshold value, iteratively decreasing the initial distance of each treatment interval to provide a revised number of sequential treatment steps, and for each one of the determined revised number of sequential treatment steps re-calculating the root force imposed on the root portion of each tooth by the given orthodontic appliance, until it is determined that the root force, of each tooth of the plurality of teeth, does not exceed the predetermined threshold value.

2. The method of claim 1, wherein determining the root force imposed on the root portion of the given tooth in the given treatment interval comprises:
   simulating movement of the given tooth within the given treatment interval, based on simulation of the movement of the given tooth from the start position to the desired end position based on the segmented 3D model of the plurality of teeth;
   determining an impact force of the given orthodontic appliance used during the given treatment interval on the given tooth, based on the simulated movement of the given tooth within the given treatment interval;
   determining the root force imposed on the root portion of the given tooth, based on the determined impact force and an anatomical consideration of the root portion of the given tooth.

3. The method of claim 2, wherein the anatomical consideration of the root portion of the given tooth comprises root portion data including one or more of: a geometry of the root portion, an indication of a length of the root portion, crown portion topography, root portion topography, root portion surface area, and type of tooth.

4. The method of claim 3, further comprising obtaining the root portion data by obtaining CT scan data of the plurality of teeth, segmenting the CT scan data to separate the individual teeth, and parsing the CT scan data to separate crown portion data from root portion data.

5. The method of claim 2, further comprising:
   determining intermediate collisions between adjacent teeth in the plurality of teeth for each treatment interval between each sequential treatment step of the initial number of sequential steps, the determining intermediate collisions being based on the determined simulated movement of each tooth.

6. The method of claim 5, further comprising displaying the determined intermediate collisions on a screen connected to the computer system.

7. The method of claim 1, wherein the re-calculating the root force imposed on the root portion of each tooth by the given orthodontic appliance comprises:
   determining a revised impact force of the given orthodontic appliance used during the given treatment interval on the given tooth, based on the simulated movement of the given tooth within the given treatment interval; and
   determining a revised root force imposed on the root portion of the given tooth, based on the revised impact force and an anatomical consideration of the root portion of the given tooth.

8. The method of claim 1, wherein the obtaining the segmented 3D model of the plurality of teeth comprises: obtaining 3D optical image data of the plurality of teeth, and digitally separating each tooth of the plurality of teeth in the 3D optical image data to obtain the segmented 3D image data of the plurality of teeth.

9. The method of claim 1, wherein the impact force of the given orthodontic appliance is determined based on Finite Element Method (FEM) modelling.

10. The method of claim 9, wherein the FEM modelling comprises imposing boundary conditions which reflect the interaction of an orthodontic appliance with the teeth, caused by contact of the teeth with the orthodontic appliance, during a simulation of the movement of the teeth from the start position to the desired end position.

11. The method of claim 1, wherein the impact force of the given orthodontic appliance is based on one or more of: orthodontic appliance material property, orthodontic appliance configuration, and orthodontic appliance method of manufacture.

12. The method of claim 1, wherein the root force comprises an average force imposed on periodontal ligaments around an entirety of the given tooth root portion.

13. The method of claim 1, wherein the decreasing the initial distance comprises decreasing the initial distance by an amount proportional to an excess amount of the determined root force above the predetermined threshold.

14. The method of claim 1, further comprising one or both of:
   displaying the determined orthodontic treatment on a screen connected to the computer system;
   sending production instructions to an orthodontic appliance manufacture apparatus, operatively connected to the processor, to generate the orthodontic appliance according to the determined orthodontic treatment.

15. The method of claim 1, wherein the obtaining a start position and a desired end position of each tooth of the plurality of teeth comprises defining the start position and the desired end position of each tooth as an x, y, z coordinate.

16. The method of claim 1, wherein the initial distance is about 200 microns.

17. A system for determining an orthodontic treatment having a number of sequential treatment steps with a given orthodontic appliance, the system comprising a computer system having a processor arranged to execute a method comprising:
   obtaining a segmented 3D model of a plurality of teeth of a patient, the segmented 3D model of each tooth of the plurality of teeth including at least crown portion data;
   obtaining a start position and a desired end position of each tooth of the plurality of teeth;
   determining an initial number of sequential treatment steps, the initial number of sequential treatment steps defining treatment intervals therebetween, to move each tooth of the plurality of teeth from the start position to the desired end position, the initial number of sequential treatment steps being based on an initial distance of each treatment interval;
   for each tooth of the plurality of teeth, and for each treatment interval, determining a root force imposed on a root portion of the tooth by the given orthodontic appliance;
   selectively executing:
      in response to the root force, of each tooth of the plurality of teeth, not exceeding a predetermined threshold value, determining that the determined initial number of sequential treatment steps is the determined orthodontic treatment; and
      in response to the root force, for any one of the teeth of the plurality of teeth, exceeding the predetermined threshold value, iteratively decreasing the initial distance of each treatment interval to provide a revised number of sequential treatment steps, and for each one of the determined revised number of sequential treatment steps re-calculating the root force imposed on the root portion of each tooth by the given orthodontic appliance, until it is determined that the root force, of each tooth of the plurality of teeth, does not exceed the predetermined threshold value.

18. The system of claim 17, further comprising one or more of:
   an imaging device communicable with the computer system for providing image data comprising at least crown portion data of the plurality of teeth, and
   orthodontic manufacturing apparatus communicable with the computer system for making at least a portion of the orthodontic appliance.

19. The system of claim 17, wherein determining the root force imposed on the root portion of the tooth in the treatment interval comprises:
   simulating movement of the tooth within the treatment interval, based on simulation of the movement of the tooth from the start position to the desired end position based on the segmented 3D model of the plurality of teeth;
   determining an impact force of the orthodontic appliance used during the treatment interval on the tooth, based on the simulated movement of the tooth within the given treatment interval;
   determining the root force imposed on the root portion of the tooth, based on the determined impact force and an anatomical consideration of the root portion of the tooth.

20. The system of claim 17, wherein the re-calculating the root force imposed on the root portion of each tooth by the orthodontic appliance comprises:
   determining a revised impact force of the orthodontic appliance used during the treatment interval on the tooth, based on the simulated movement of the tooth within the treatment interval; and
   determining a revised root force imposed on the root portion of the tooth, based on the revised impact force and the anatomical consideration of the root portion of the tooth.

* * * * *